United States Patent
Wolst et al.

(10) Patent No.: US 8,833,141 B2
(45) Date of Patent: Sep. 16, 2014

(54) SENSOR ELEMENT OF A GAS SENSOR AND METHOD FOR OPERATING THE SAME

(75) Inventors: Oliver Wolst, Singapore (SG); Stefan Henneck, Leonberg (DE); Markus Widenmeyer, Schoenaich (DE); Alexander Martin, Regensburg (DE)

(73) Assignee: Robert Bosch GmbH, Stuttgart (DE)

( * ) Notice: Subject to any disclaimer, the term of this patent is extended or adjusted under 35 U.S.C. 154(b) by 210 days.

(21) Appl. No.: 13/138,288

(22) PCT Filed: Dec. 15, 2009

(86) PCT No.: PCT/EP2009/067160
§ 371 (c)(1),
(2), (4) Date: Oct. 7, 2011

(87) PCT Pub. No.: WO2010/091761
PCT Pub. Date: Aug. 19, 2010

(65) Prior Publication Data
US 2012/0017665 A1    Jan. 26, 2012

(30) Foreign Application Priority Data
Feb. 12, 2009 (DE) .......................... 10 2009 000 820

(51) Int. Cl.
*G01N 7/00* (2006.01)
*G01N 27/414* (2006.01)
*G01N 33/00* (2006.01)

(52) U.S. Cl.
CPC .......... *G01N 27/414* (2013.01); *G01N 33/0013* (2013.01)

USPC ......................................... 73/31.06; 73/31.05

(58) Field of Classification Search
CPC .......................... G01N 27/414; G01N 27/4074
USPC .............................................. 73/31.05, 31.06
See application file for complete search history.

(56) References Cited

U.S. PATENT DOCUMENTS

| 4,840,913 | A |  | 6/1989 | Logothetis et al. |
| 5,866,075 | A |  | 2/1999 | Gupta et al. |
| 5,948,323 | A | * | 9/1999 | McLaughlin et al. ........ 252/610 |
| 6,165,336 | A |  | 12/2000 | Maki et al. |
| 6,883,364 | B2 |  | 4/2005 | Sunshine et al. |
| 7,127,935 | B2 | * | 10/2006 | Bonne et al. .................... 73/23.2 |
| 2005/0167409 | A1 | * | 8/2005 | Knorr et al. .............. 219/121.85 |
| 2006/0113199 | A1 |  | 6/2006 | Sasaki et al. |
| 2006/0289308 | A1 | * | 12/2006 | Shaddock et al. ............ 204/424 |
| 2007/0033929 | A1 | * | 2/2007 | Telford et al. ................... 60/287 |
| 2008/0072551 | A1 | * | 3/2008 | Zuberi ......................... 55/385.1 |
| 2009/0193790 | A1 | * | 8/2009 | Richter et al. .................. 60/274 |

FOREIGN PATENT DOCUMENTS

| DE | 43 39 737 | 1/1995 |
| DE | 195 19 189 | 9/1996 |
| DE | 197 08 770 | 8/1998 |
| DE | 199 16 798 | 11/2000 |

(Continued)

*Primary Examiner* — Hezron E Williams
*Assistant Examiner* — David Z Huang
(74) *Attorney, Agent, or Firm* — Kenyon & Kenyon LLP (57) ABSTRACT

A sensor element of a gas sensor for determining gas components in gas mixtures includes a field effect transistor and/or a diode which has a current flow which changes upon contact with a gas to be detected, and which is positioned in a manner protected, by a protective cap, from direct access by the gas mixture. The protective cap has a heating element, a glass former, and/or an oxidation catalyst.

15 Claims, 4 Drawing Sheets

(56) References Cited

FOREIGN PATENT DOCUMENTS

| | | |
|---|---|---|
| DE | 10 2005 010 032 | 9/2006 |
| DE | 10 2006 039 964 | 2/2008 |
| DE | 10 2007 040 726 | 3/2009 |
| EP | 0 604 468 | 7/1994 |
| JP | 55-58448 | 5/1980 |
| JP | 58-92846 | 6/1983 |
| JP | 63-158444 | 7/1988 |
| JP | 1-107142 | 4/1989 |
| JP | 8-226908 | 9/1996 |
| JP | 8-247984 | 9/1996 |
| JP | 11-142356 | 5/1999 |
| JP | 11-211688 | 8/1999 |
| JP | 2003-270181 | 9/2003 |
| JP | 2004-20275 | 1/2004 |
| JP | 2006-126160 | 5/2006 |
| JP | 2006-153595 | 6/2006 |
| JP | 2006-306673 | 11/2006 |
| JP | 2007-512514 | 5/2007 |
| JP | 2007-292736 | 11/2007 |
| WO | WO 96/37771 | 11/1996 |

* cited by examiner

SENSOR ELEMENT OF A GAS SENSOR AND METHOD FOR OPERATING THE SAME

BACKGROUND OF THE INVENTION

1. Field of the Invention

The present invention relates to a sensor element of a gas sensor for determining gas components in gas mixtures, to a method for operating the same.

2. Description of Related Art

Gas-sensitive semiconductor-based field effect transistors are used to detect substances contained in a fluid stream, in particular gases in a gas stream. In general, impingement of the substance to be detected, for example a gas or a liquid or a gas or liquid mixture, results in a change in channel impedance and thus in a change in the current (called the "channel current") flowing through the field effect transistor from the source electrode to the drain electrode. If semiconductor materials having a large band gap, i.e. a band gap of more than 3 eV, are used, for example such as gallium nitride or silicon carbide, this makes it possible, in principle, to use the gas-sensitive field effect transistors for sensor applications at temperatures up to 800° C.

At the selected working point of the gas-sensitive field effect transistor, the channel current without impingement of the substance to be detected (corresponding what is called a "null signal" or "offset") is higher, often by orders of magnitude of usually 103, than the change in channel current resulting from impingement of a substance to be detected. Because of the poor signal-to-offset ratio, this imposes difficult requirements in terms of current measurement. A further problem which results is that the offset can be influenced by external interference effects. External interference effects are produced, for example, by temperature changes or by sensor degradation, which are not based on the presence of substances to be detected. Because of the signal-to-offset ratio that exists, the change in channel current resulting from interference effects can be of the same order of magnitude as, or in the most unfavorable case even greater than, the change occurring due to the presence of the substance to be detected. Because interference effects cannot be entirely precluded, the associated error in the measured signal is large, and in the worst case prevents sufficiently accurate determination of the substance to be detected.

U.S. Pat. No. 6,883,364 discloses the use of, inter alia, field effect transistors as sensors in handheld devices for detecting gases. Gas-sensitive resistors (called "chemoresistors") are usually used here. The sensors used are, however, not suitable for drift compensation and for compensating for the offset of the chemoresistors.

Also known, from U.S. Pat. No. 6,165,336, are gas sensors that are constructed, for example, on the basis of a semiconductor gas sensor and that have a porous ceramic layer as a gas-permeable protective element in order to prevent the access of harmful gases.

BRIEF SUMMARY OF THE INVENTION

An object of the present invention is to make available a protective element for gas sensors that not only prevents the access of harmful substances to a sensor element of a gas sensor, but additionally renders those harmful substances harmless.

The sensor element of the gas sensor has for this purpose, for example, a protective cap that prevents direct access by the gas mixture to be determined to the surface of the sensor element, and that has a heating means, a glass former, and/or an oxidation catalyst.

The particular advantage of this embodiment may be seen in the fact that, for example, soot that becomes deposited on the protective cap can be effectively removed by the operation of a heating means or the existence of an oxidation catalyst. As a result of the alternative or additional existence of a glass former in the region of the protective cap, harmful components contained in the gas mixture to be determined, such as e.g. alkali or alkaline-earth compounds that result from road salt or as material abraded from the engine block of an internal combustion engine or corresponding drive pistons, can be captured. Without protective measures, these result in deposits or buildups in the region of the sensor element, and consequently to the formation of so-called electron traps that cause electrical transient effects which are expressed in the form of a non-constant channel current or signal current, and cause an unstable sensor element offset current. Lack of stability in the offset current results in a low-accuracy sensor signal.

If the claimed sensor element serves for the determination of exhaust gases of internal combustion engines, perceptible concentrations of silicon compounds can additionally be identified in such exhaust gases. In extreme cases, these compounds result in vitrification of the electrodes of the sensor element, so that they exhibit insufficient sensitivity to the gas components that are being determined. If, on the other hand, the protective cap of the sensor element has a glass former, for example as a coating or as a material component, the aforesaid interfering substances are then, because of the getter property of the glass former, permanently bound in the region of the protective cap by physical effects or by corresponding chemical reactions.

It is advantageous, for example, if the protective cap is embodied from a ceramic, and is secured on the sensor element by way of a glass solder. This embodiment ensures that the sensor element according to the present invention has a high level of temperature resistance, and thus creates the capability of investigating combustion exhaust gases with regard to their composition.

It is further advantageous if a titanate, a silicate, a borate, or a phosphate is used as a glass former. The advantage of using these substances is that they are available on an industrial scale, and can easily be applied onto the protective cap using a corresponding impregnation process.

It is further advantageous if the protective cap of the sensor element has a multi-layer construction, a first layer applied onto the protective cap being constituted by a glass former and a further layer that has an oxidation catalyst being located on this first layer containing a glass former. Both soot contained in a combustion exhaust gas, and ionic contaminants, can thereby be effectively captured.

The application of an oxidation catalyst furthermore makes it possible to embody the sensor element in a manner sensitive to, for example, nitrogen oxides, since oxidizable gas components present in a gas mixture, such as hydrocarbons, hydrogen, or nitric oxide or nitrous oxide, can be oxidized to carbon dioxide, water, or nitrogen dioxide respectively. Only nitrogen dioxide is thus present, as a gas component to be detected, in a gas mixture that reaches the sensitive region of the gas sensor; the water and carbon dioxide that are likewise formed do not interfere with determination thereof.

It is furthermore advantageous if the protective cap of the sensor element according to the present invention is always heated when a certain level of contamination with, for example, soot or other combustible particles is present. This can advantageously be detected by, for example, sensing the time delay between the occurrence, or a change in the concentration, of a gas component within the gas mixture, and the detection thereof by way of the sensor element, and comparing it with a predefined maximum time delay. If that maximum time delay is exceeded, heating of the protective cap of the sensor element is automatically initiated, and any deposit of combustible particles is thereby removed from it.

The sensor element according to the present invention, and the method for operating the same, are advantageously suitable for determining gas components in exhaust gases of internal combustion engines, power plant facilities, or heating units. In the field of exhaust gas post-treatment, a further potential application consists in monitoring the functionality of NOX storage catalysts or SCR exhaust gas post-treatment systems.

DETAILED DESCRIPTION OF THE INVENTION

Figure 1:
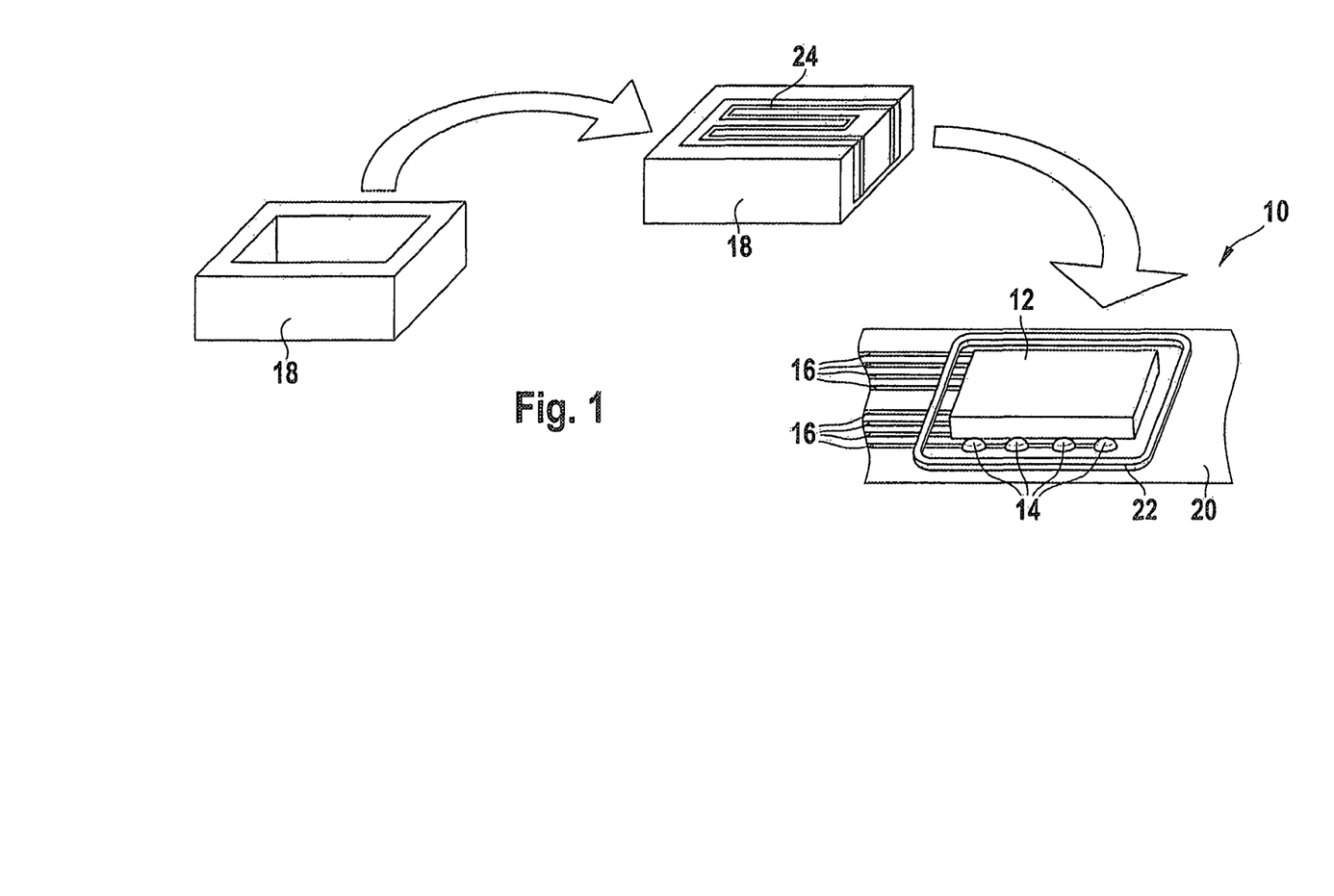
FIG. 1 shows a schematic method sequence during manufacture of a sensor element according to the present invention.
Figure 2:
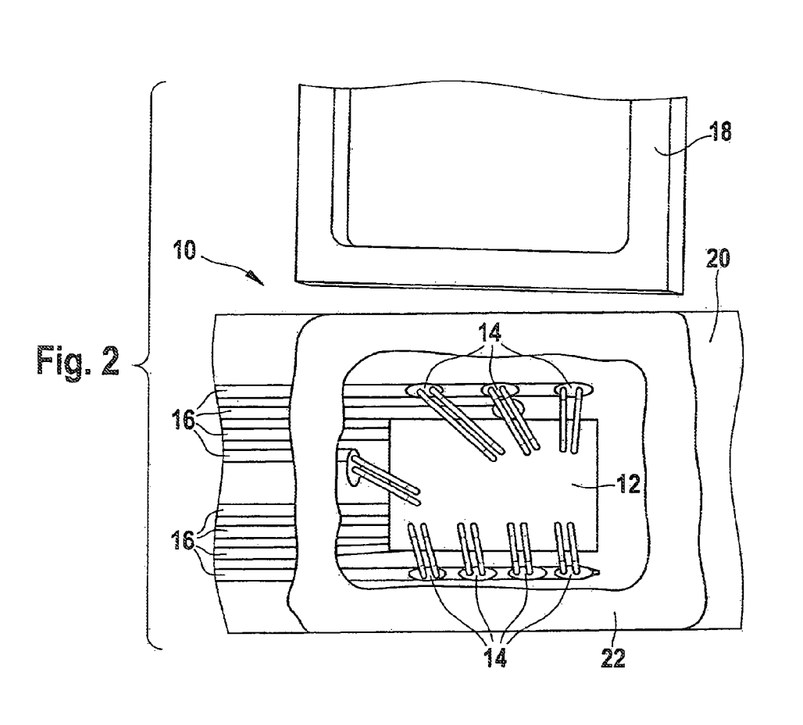
FIG. 2 is a plan view of a sensor element during the manufacturing process.

FIGS. 1 and 2 show a sensor element on which the invention is based, during its manufacture.

Sensor element 10 according to the present invention encompasses a substrate 12 on which are provided, for example, at least one, preferably multiple gas-sensitive detection units 28. The gas-sensitive detection units are preferably embodied on the basis of a semiconductor pattern and can in that context be embodied, for example, as a field effect transistor in the form of a MOSFET or CHEMFET or, for example, as semiconductor diodes. The gas-sensitive detection units disposed on substrate 12 are connected, for example via contacting areas 14 and conductor path patterns 16, to a corresponding signal evaluation structure that is not depicted in the Figures.

Contacting areas 14 serve, for example for electrical contacting of the source and drain electrodes of the individual field effect transistors, and for application of control to the respective gate electrodes. Multiple gas-sensitive detection units are preferably disposed on substrate 12, so that they can be interconnected with one another to form a so-called "electronic nose." Each of the gas-sensitive detection units disposed on substrate 12 preferably senses a different gas component of a gas mixture to be determined, or a different group of gas components present in a gas mixture.

In order to allow the longevity of sensor element 10 to be utilized, for example in continuous operation when investigating exhaust gases of internal combustion engines, substrate 12 is protected, for example with a ceramic protective cap 18, preferably completely from direct access by the gas mixture to be determined. Ceramic protective cap 18 is embodied for this purpose, for example, in the form of a cuboid open on one large surface. In order to ensure a permanent connection of ceramic protective cap 18 to a carrier element 20 carrying substrate 12, carrier element 20 is equipped, for example, with a glass solder 22, and ceramic protective cap 18 is slipped with its open side over substrate 12 and pressed together with carrier element 20 in such a way that glass solder 22 connects and secures protective cap 18 to carrier element 20 in gas-tight fashion. A concluding heat treatment process produces a permanent connection between protective cap 18 and carrier element 20 of sensor element 10.

Figure 3:
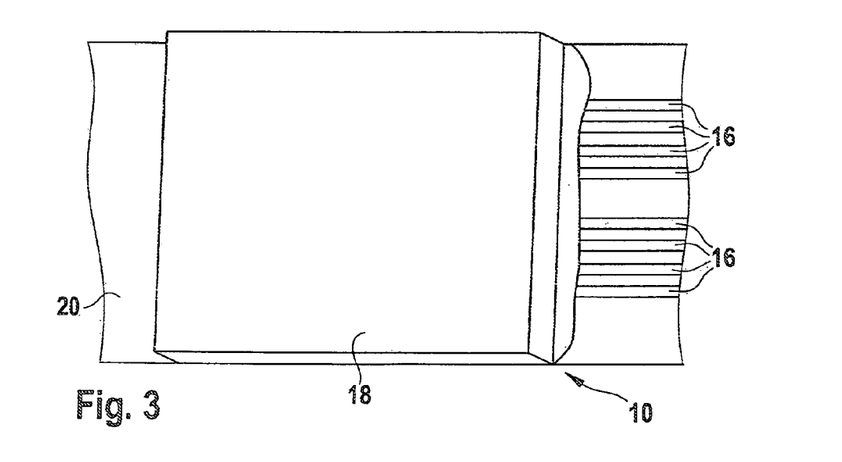
FIG. 3 is a plan view of a completed sensor element.

Sensor element 10 that has been completed in this fashion is depicted, for example, in FIG. 3, in which identical reference characters refer to the same components as in FIGS. 1 and 2.

In order to ensure access to the respective gas-sensitive detection units of sensor element 10 by the gas components to be determined of a gas mixture that is being investigated, ceramic protective cap 18 is embodied, for example, from a porous material, in particular having open pores. It is thereby possible to prevent access by particles or aerosols entrained in a gas mixture, whereas access to the gas-sensitive detection units of sensor element 10 by gas components to be investigated is ensured.

In addition, a high signal quality for sensor element 10 is ensured in particular when protective cap 18 is embodied so that substrate 12 is surrounded as completely as possible by protective cap 18, and the additionally enclosed air volume between substrate 12 and protective cap 18 is minimized. For example, the gas volume enclosed between protective cap 18 and substrate 12 is equal to 0.0001 μm to 1 ml, preferably 0.0005 to 10 μl, and in particular 0.001 to 0.003 μl. It is furthermore advantageous if the wall thickness of ceramic protective cap 18 is embodied in such a way that there is as little perceptible interference as possible with the diffusion behavior of gas components to be determined. For that purpose, the wall thickness of ceramic protective cap 18 is equal to, for example, 2 μm to 5 mm, preferably between 10 and 200 μm, and in particular between 20 and 80 μm.

In addition, protective cap 18 is fabricated, for example, from the same ceramic material as carrier element 20 on which substrate 12 is positioned. The result is that in a context of alternating temperature stresses, the thermal expansion behavior to observed in ceramic protective cap 18 and in carrier 20 is largely comparable. This moreover allows the use of a glass solder or other ceramic adhesive to connect ceramic protective cap 18 to carrier element 20. In principle, however, ceramic materials having a differing composition can also be used, provided they exhibit thermal expansion behavior, or a coefficient of thermal expansion, that is comparable to that of the ceramic material of carrier element 20. Zirconium dioxide, for example, which can be used in partly or entirely stabilized form, is thus suitable as a ceramic material for protective cap 18 or carrier element 20. Also suitable as alternative ceramic materials of protective cap 18 are low-temperature co-fired ceramics (LTCC), as well as glass-fiber-sintered aluminum oxide ceramics or cordierite.

Protective cap 18 is manufactured by, for example, processing corresponding green films of ceramic material by laminating multiple plies and then milling out the desired honeycomb-shaped geometry to yield a ceramic green compact. In order to achieve a high level of open porosity for the ceramic in the sintered state, the green compact is sintered, for example below a final sintering temperature of the ceramic, for a longer period of, for example, one hour, with which an open porosity of, for example, 30 to 38, in particular 34 vol % can be achieved.

If zirconium dioxide, for example, is used as a ceramic material, the temperature during heat treatment is then between 1150 and 1200° C., although final sintering is to be expected only at a temperature from 1380 to 1400° C. In addition, an open-pore structure in the sintered ceramic can be ensured by additionally enriching the material of the green compact with organic, for example powdered material that is burned out during heat treatment and results in a porous structure.

Alternative methods for shaping the green compact that constitutes protective cap 18 involve the utilization of micro-injection molding, stamping, and then punching out from green ceramic films, or a drying process.

In order to manufacture sensor element 10, firstly the corresponding gas-sensitive detection units in the form of chemosensitive field effect transistors or semiconductor patterns are mounted, for example in a joining process, onto substrate 12, which can be embodied e.g. from zirconium dioxide. The positioned gas-sensitive detection units are then contacted, for example using the flip-chip technique or by way of bonding wire connections, and lastly protective cap 18 is placed onto a ring of glass solder previously positioned on carrier element 20. Drying of the glass solder paste is then performed, and preferably a heat treatment that results in melting of the glass, thereby ensuring permanent attachment of ceramic protective cap 18 onto ceramic carrier element 20. It is advantageous in this context if the glass solder used is a glass that at least partly crystallizes during the heat treatment process, since this ensures subsequent long-term durability of sensor element 10 even at high operating temperatures.

Because soot and aerosols settle onto the surface of sensor element 10 or onto the surface of ceramic protective cap 18 over time during continuous operation of sensor element 10, in particular when investigating combustion exhaust gases, according to a first embodiment said cap is provided, for example, with an electrical resistance pattern. This can encompass, for example, a serpentine resistive conductor path that, upon application of a corresponding heating voltage, results in heating of protective cap 18. The serpentine resistive conductor path 24 can cover the surface of ceramic protective cap 18 at least partly, or also over its entire area.

Contacting to resistive conductor path 24 is accomplished, for example, by way of conductor path pattern 16. When a sufficient high coverage of the surface of ceramic protective cap 18 with deposits, soot, or aerosols is detected, a heating voltage is at least briefly applied to resistive path 24 so that ceramic protective cap 18 heats up, for example, to a temperature greater than 600° C. At this temperature, combustible soot constituents that have become deposited onto the surface of ceramic protective cap 18 are combusted, and correspondingly deposited aerosols are vaporized.

The possibility exists of carrying out the heating of ceramic protective cap 18, for example, on a regular basis for a predefined period of time. In order to avoid unnecessary energy consumption for the heating of ceramic protective cap 18, however, the heating of resistive conductor path 24 can also be performed whenever a sufficient coverage of ceramic protective cap 18 with undesired constituents of the gas mixture is detected. The time delay between the occurrence of a change in the concentration of a gas component to be detected, and the point in time at which that change in concentration is detected, can be utilized, for example, for this purpose.

As ceramic protective cap 18 becomes covered with undesired constituents, this time difference increases with increasing coverage of the surface of ceramic protective cap 18 with corresponding components that prevent the diffusion into the interior of sensor element 10 of gas components that are to be detected. If the time delay between the change in the concentration of a gas component and detection thereof by sensor element 10 therefore exceeds a predefined threshold value that is, for example, stored in a corresponding control device, then heating of the porous ceramic protective cap 18 can, for example, be authorized when that threshold value is exceeded.

For example, in an exhaust gas system that provides, for example, actions to decrease nitrogen oxides in combustion exhaust gases, an artificially elevated concentration of ammonia in the gas mixture to be determined can be utilized to determine the time difference between the occurrence of the ammonia in the gas mixture to be determined and detection of the ammonia by sensor element 10, in order to monitor the loading of ceramic protective cap 18 with undesired constituents. In exhaust gas systems that encompass, for example, a nitrogen oxide storage catalyst (NSC), it is possible to resort, for example, to an overmetering of fuel to the corresponding internal combustion engine, and to utilize the time difference between the occurrence of gaseous residual fuel components in the gas mixture to be determined (or the occurrence of an oxygen deficit in the combustion exhaust gas), and detection thereof, as a parameter for determining the loading of ceramic protective cap 18.

Particularly high signal accuracy for sensor element 10 is observed, however, if the heating of ceramic protective cap 18 is performed at least largely continuously. Because, for thermophoretic reasons, very few soot particles become deposited on particularly hot surfaces, and any soot that does become deposited is immediately combusted oxidatively, it may be assumed that the diffusion behavior of gas components to be determined into the interior of sensor element 10 to the gas sensitive detection units of sensor element 10 is constantly stable.

According to a second embodiment of the present invention, ceramic protective cap 18 can additionally or alternatively be provided with a chemical oxidation function. For this, the material of ceramic protective cap 18 can, for example, be impregnated with one or more substances functioning as oxidation catalysts. A corresponding embodiment is depicted, for example, in FIG. 4. The porous ceramic structure of ceramic protective cap 18, constituted by ceramic particles 30, is applied, for example, by corresponding skimming, blade-coating, soaking, misting, spraying, immersion, or aspiration of, or by passage through, a solution or suspension or dispersion containing the catalyst material.

Corresponding impregnation processes can also be performed, for example incipient wetness, soaking, or chemisorption from a solution having a corresponding pH, or by precipitation of, for example, poorly soluble metal hydroxides or metal carbonates of metal salts such as nitrates, halides, carbonates, or acetates.

According to a further embodiment, substances functioning as an oxidation catalyst can also be applied onto the porous protective cap 18 in the form of an additional layer, in the form of a washcoat suspension, e.g. by skimming, immersion, aspiration, etc. The thickness of the layer is equal, for example, to 1 μm to 5 mm, preferably between 10 and 1000 μm.

Provision is then made, for example, for a drying step at, for example, 50 to 500° C., and subsequent to that a heat treatment process at a temperature from, for example, 350 to 700° C. This occurs, if applicable, in a correspondingly selected calcination atmosphere, for example a hydrogen/nitrogen atmosphere, in which context the catalyst precursor compounds are converted into a catalytically active, for example, elemental form. If the catalytically active substances are applied in the form of a washcoat formulation, this then ensures that the ceramic particles are sintered onto the material of the porous protective cap 18.

In order to achieve sufficient loading of the ceramic material of ceramic protective cap 18 with catalytically active material, the process sequence of impregnation, drying, and calcination can also carried out several times in succession until a loading of the ceramic material of protective cap 18 of, for example, 0.1 to 50 weight percent, preferably 2 to 20 weight percent, is achieved. Noble metals such as platinum, palladium, or rhodium, or mixtures thereof, are used, for example, as catalytically active substances functioning as oxidation catalysts.

Because only combustible contaminants of protective cap 18 can be removed by heating protective cap 18 or by the existence of oxidation catalysts in the material thereof, but mineral contaminants cannot be sufficiently immobilized, the material of ceramic protective cap 18 alternatively or additionally encompasses a so-called getter material. This serves in general fashion to immobilize undesired substances that can be a constituent of the gas mixture to be determined, but that can result in inactivation of the gas-sensitive detection units of sensor element 10. These are, for example, alkali- or alkaline earth-containing substances that can result, for example, from road salt, or magnesium- or iron-containing compounds that can result from material abraded from the piston or engine block of a corresponding internal combustion engine. Further mineral contaminants are aluminum- and silicon-containing compounds that can be produced, for example, from contamination with engine oil.

The getter materials used in the context of the present invention are, for example, glass formers. These can be, for example, mixed as a doping agent into the material of the green compact used for the manufacture of ceramic protective cap 18. A further possibility, however, is to introduce corresponding glass formers after the completion of protective cap 18, via an impregnation process such as the one already described for introduction of the catalytically active substances functioning as oxidation catalysts. Suitable getter materials or glass formers are, for, example, compounds such as aluminum oxide, or aluminum oxide hydrates such as bohmite, titanates, silicates, aluminosilicates, magnesium aluminosilicates such as, for example, cordierite, borates, phosphates, in particular rare earth phosphates such as monazite having the composition [Ce, La, Nb]PO4, or mixtures thereof.

Figure 4:
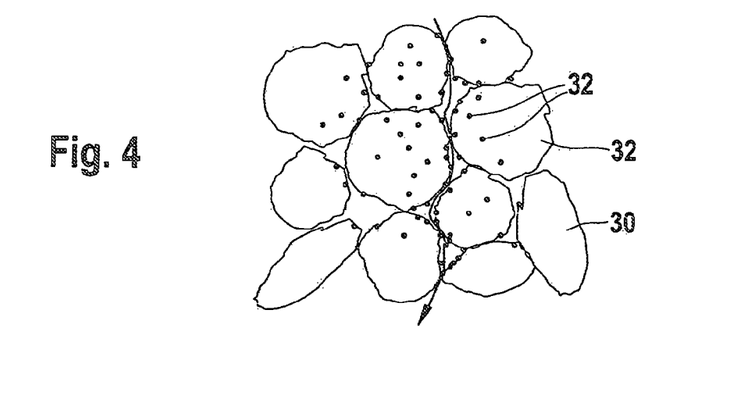
FIG. 4 schematically depicts a portion of the material of a protective cap of the sensor element, according to a first embodiment.
Figure 5:
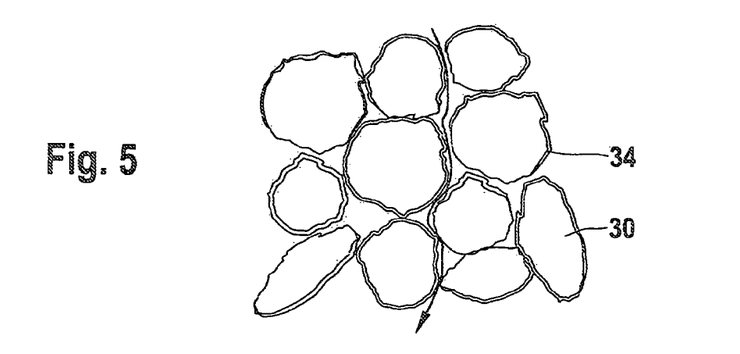
FIG. 5 schematically depicts a portion of the material of a protective cap of the sensor element, according to a second embodiment.
Figure 6:
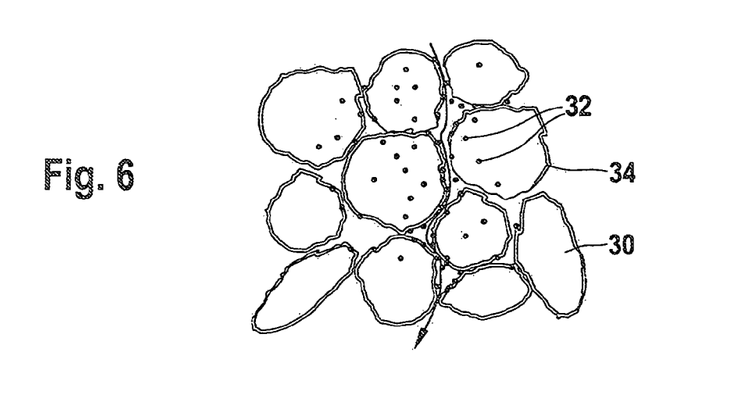
FIG. 6 schematically depicts a portion of the material of a protective cap of the sensor element, according to a third embodiment.

The porous ceramic structure of protective cap 18 is always configured in such a way that corresponding diffusion channels for the gas mixture to be determined, which are illustrated in FIGS. 4 to 6 by corresponding arrows, are not interrupted. If a corresponding glass-forming material is introduced via an impregnation process into the porous structure of protective cap 18, it forms, for example, the layer structure depicted in FIG. 5. In this context, the ceramic particles 30 are covered, for example, with a coating 34 of a glass former.

An advantageous embodiment of a sensor element 10 provides for a combination of the embodiments depicted in FIGS. 4 and 5 of the material of a ceramic protective cap 18. This embodiment is depicted in FIG. 6: onto a layer of glass former 34, particles 32 of a catalytically active material, functioning as an oxidation catalyst, are applied onto ceramic particles 30. This two-layer configuration ensures on the one hand the immobilization of mineral contaminants, and on the other hand also oxidative elimination of combustible constituents that arrive in the region of ceramic protective cap 18 by way of the gas mixture to be determined.

Figure 7:
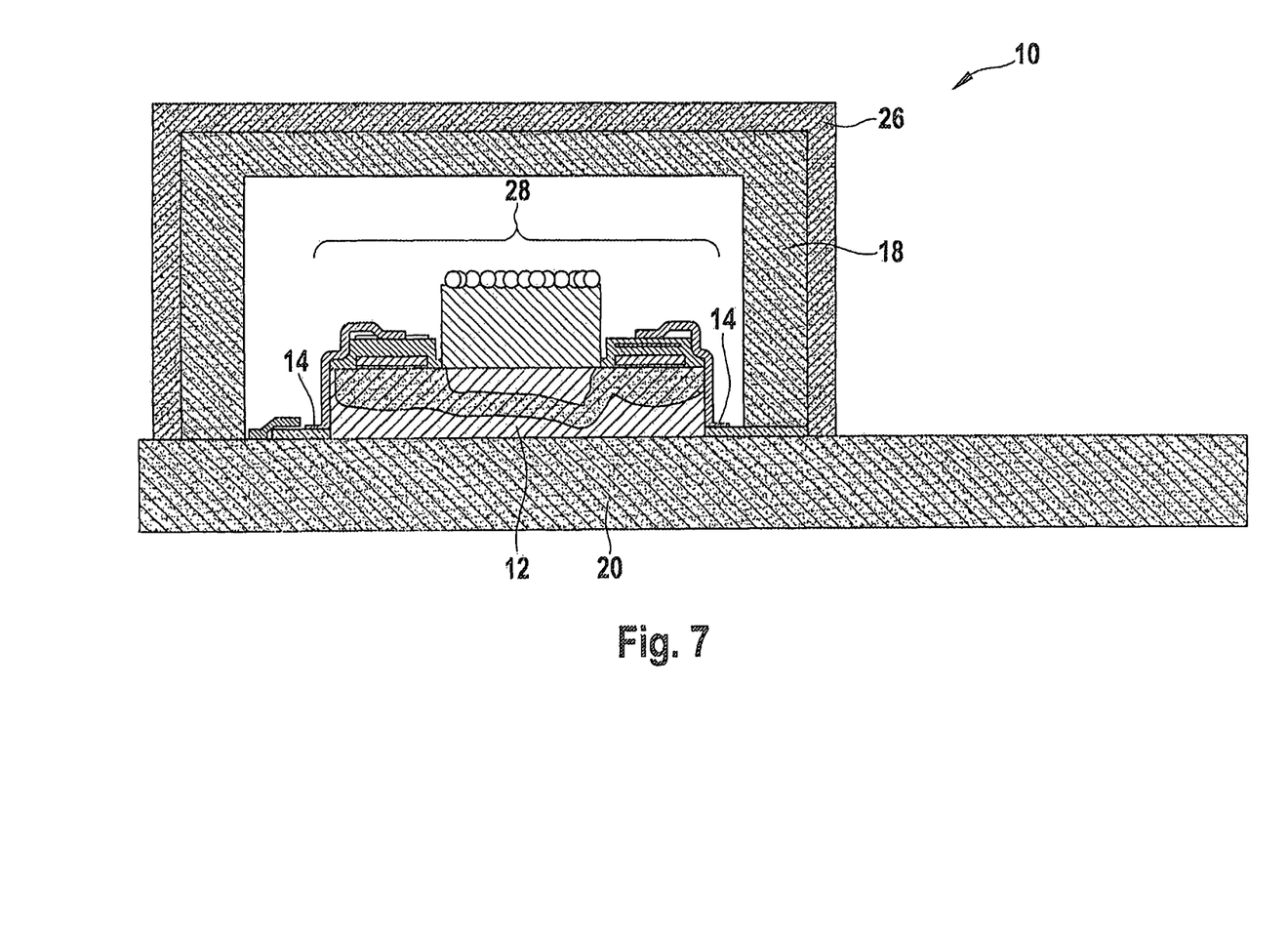
FIG. 7 is a schematic sectioned depiction of a sensor element according to the present invention.

FIG. 7 is a sectioned depiction of a sensor element according to the present invention in completed form; identical reference characters refer to the same components as in FIGS. 1 to 6.

Sensor element 10 has, for example, a porous protective cap 18 that has an additional layer 26 containing an oxidation catalyst. Additional layer 26 is embodied from ceramic particles made, for example, from aluminum oxide, zirconium dioxide, or silicon dioxide, or mixtures thereof, which are coated on the surface with substances functioning as an oxidation catalyst. Additional layer 26 is present as a substantially crack-free, porous layer.

Alternatively, it is possible to immerse the entire sensor element 10, for example, into a washcoat solution of a substance functioning as an oxidation catalyst, and thereby to equip both protective cap 18 and carrier element 20 with an additional layer 26.

Additional embodiments of a ceramic protective cap 18 can contain further protective layers based on oxides of the fourth, fifth, or sixth subgroup of the periodic table of the elements, for example zirconium dioxide, titanium dioxide, hafnium dioxide, niobium oxides, tungsten oxides. A further possibility is to provide protective layers based on cerium oxides or lanthanum oxides, or based on perovskites. The aforesaid compounds are suitable as oxygen-storing compounds, and can thus participate in supporting fashion in the oxidative elimination of combustible contaminants of protective cap 18.

What is claimed is:

1. A sensor element of a gas sensor for determining gas components in a gas mixture, comprising:
    at least one of a field effect transistor and a diode having a current flow which changes upon contact with a gas to be detected;
    a protective cap positioned relative to the at least one of the field effect transistor or the diode in such a manner to protect the at least one of the field effect transistor or the diode from direct access by the gas mixture, wherein the protective cap includes a heating element that removes contaminating particles from a surface of the protective cap by burning the contaminating particles; and
    a control device that activates the heating element by:
        detecting a time delay between (i) one of an occurrence of a gas component in the gas mixture or a change in the concentration of the gas component within the gas mixture, and (ii) detecting by the sensor element the one of the gas component or the change in the concentration of the gas component;
        comparing the detected time delay with a predefined maximum time delay; and
        activating the heating element to heat the protective cap if the detected time delay exceeds the predefined maximum time delay.

2. The sensor element as recited in claim 1, wherein the protective cap is made of a porous ceramic.

3. The sensor element as recited in claim 2, wherein the protective cap is secured to a carrier element by a glass solder.

4. The sensor element as recited in claim 3, wherein the heating element is a resistance heating element.

5. The sensor element as recited in claim 3, wherein the protective cap includes a glass former that is one of a titanate, a silicate, a borate, or a phosphate.

6. The sensor element as recited in claim 5, wherein the glass former makes up a weight proportion from 5 to 25 wt % of the material of the protective cap.

7. The sensor element as recited in claim 3, wherein the protective cap includes an oxidation catalyst that contains one of platinum, rhodium, palladium, a perovskite, a cerium oxide, or a lanthanum oxide.

8. The sensor element as recited in claim 7, wherein the oxidation catalyst makes up a weight proportion from 0.1 to 50 wt % of the material of the protective cap.

9. The sensor element as recited in claim 8, wherein the oxidation catalyst is applied onto a coating containing a glass former.

10. The sensor element as recited in claim 9, wherein the oxidation catalyst is contained in an additional layer at least partly covering the protective cap.

11. A method for operating a sensor element of a gas sensor for determining gas components in a gas mixture, the sensor element including at least one of a field effect transistor or a diode having a current flow which changes upon contact with a gas to be detected, and a protective cap positioned to protect the at least one of the field effect transistor or the diode from direct access by the gas mixture, wherein the protective cap includes at least one of a heating element, a glass former, or an oxidation catalyst, the method comprising:

detecting a time delay between (i) one of an occurrence of a gas component in the gas mixture or a change in the concentration of the gas component within the gas mixture, and (ii) detecting by the sensor element the one of the gas component or the change in the concentration of the gas component;

comparing the detected time delay with a predefined maximum time delay; and heating the protective cap if the detected time delay exceeds the predefined maximum time delay.

12. The method as recited in claim 11, wherein the detection of the time delay is made during use of the sensor element, by adding to the gas mixture an elevated quantity of at least one of ammonia or a hydrocarbon-based fuel.

13. The method as recited in claim 11, wherein the method is used to determine a gas component in exhaust gases of one of internal combustion engines, power plant facilities, or heating units.

14. The method as recited in claim 11, wherein the method is used to monitor the functionality of one of an NOx storage catalyst or an SCR exhaust gas post-treatment system.

15. A sensor element of a gas sensor for determining gas components in a gas mixture, comprising:

at least one of a field effect transistor and a diode having a current flow which changes upon contact with a gas to be detected; and a protective cap positioned relative to the at least one of the field effect transistor or the diode in such a manner to protect the at least one of the field effect transistor and or the diode from direct access by the gas mixture, wherein the protective cap includes a glass former as a getter material that immobilizes contaminants contained in the gas.

* * * * *